(12) United States Patent
Ziegler et al.

(10) Patent No.: US 6,596,516 B2
(45) Date of Patent: Jul. 22, 2003

(54) PROCESS FOR THE FERMENTATIVE PREPARATION OF L-AMINO ACIDS USING CORYNEFORM BACTERIA

(75) Inventors: Petra Ziegler, Aachen (DE); Lothar Eggeling, Jülich (DE); Hermann Sahm, Jülich (DE); Georg Thierbach, Bielefeld (DE); Walter Pfefferle, Halle (DE)

(73) Assignees: Degussa AG, Dusseldorf (DE); Forschungszentrum Jülich GmbH, Jülich (DE)

( * ) Notice: Subject to any disclaimer, the term of this patent is extended or adjusted under 35 U.S.C. 154(b) by 66 days.

(21) Appl. No.: 09/731,826

(22) Filed: Dec. 8, 2000

(65) Prior Publication Data

US 2002/0072098 A1 Jun. 13, 2002

(30) Foreign Application Priority Data

Dec. 9, 1999 (DE) .......................... 199 59 329

(51) Int. Cl.$^7$ .......................... C12P 13/04; C12P 13/06; C12P 13/08; C12N 15/01; C12N 1/21
(52) U.S. Cl. .................... 435/106; 435/41; 435/175; 435/440; 435/471; 435/476; 435/477; 435/320.1; 435/243; 435/252.1; 435/252.3; 435/260; 536/24.1; 536/23.1
(58) Field of Search .................... 435/41, 106, 115, 435/440, 471, 476, 477, 320.1, 243, 252.1, 252.3, 260; 536/22.1, 23.1, 24.1

(56) References Cited

FOREIGN PATENT DOCUMENTS

| EP | 0 204 326 A2 | 12/1986 |
|---|---|---|
| EP | 0 205 849 A2 | 12/1986 |
| EP | 0 338 790 A2 | 10/1989 |
| JP | 8-107788 | 4/1996 |

OTHER PUBLICATIONS

Bailey Toward a science of metabolic engineering pp. 1668–1675 vol. 252 1991.*
Bono et al. Reconstruction of amino acid biosynthesis pathways from the complete genome sequence pp. 203–210 1998.*
Malumbres et al. Molecular control mechanisms of lysine and threonine biosynthesis in amino acid–producing coryebacteria: redirecting carbon flow pp. 103–114 1996.*

Braus Aromatic amino acid biosynthesis in the yeast *saccharomyces cerevisiae*: a model system for the regulation of a eukaryotic biosynthetic pathway pp. 349–370 1991.*

S. Graupner, "Cloning Vector pYannil, Complete Sequence," XP002165529, Database Embl 'Online! accession: AJ247369, Jun. 30, 1999.

Ziegler Petra, "Secretion and degradation of L–threonine in *Corynebacterium glutamicum*," XP002165538, Database Chemabs 'Online!, accession: 2001:213630.

European Search Report in foreign counterpart appln. No. EP 00 71 0033, dated Apr. 26, 2001.

* cited by examiner

*Primary Examiner*—David Guzo
*Assistant Examiner*—David A. Lambertson
(74) *Attorney, Agent, or Firm*—Smith, Gambrell & Russell

(57) ABSTRACT

A process for the preparation of L-amino acids, in which the following steps are carried out, a) fermenting the desired L-amino acid-producing bacteria in which at least the glyA gene is attenuated, in particular by removal of the natural promoter, and optionally b) concentrating the desired product in the medium or in the cells of the bacteria and c) isolating the L-amino acid, and optionally bacteria in which further genes of the biosynthesis pathway of the desired L-amino acid are additionally amplified are employed, or bacteria in which the metabolic pathways which reduce the formation of the desired L-amino acid are at least partly eliminated are employed, and nucleotide sequences of the lacI-tac-5'glyA or lacI-tac-glyA unit.

12 Claims, 1 Drawing Sheet

Figure 1: Map of the plasmid pK18mobglyA'
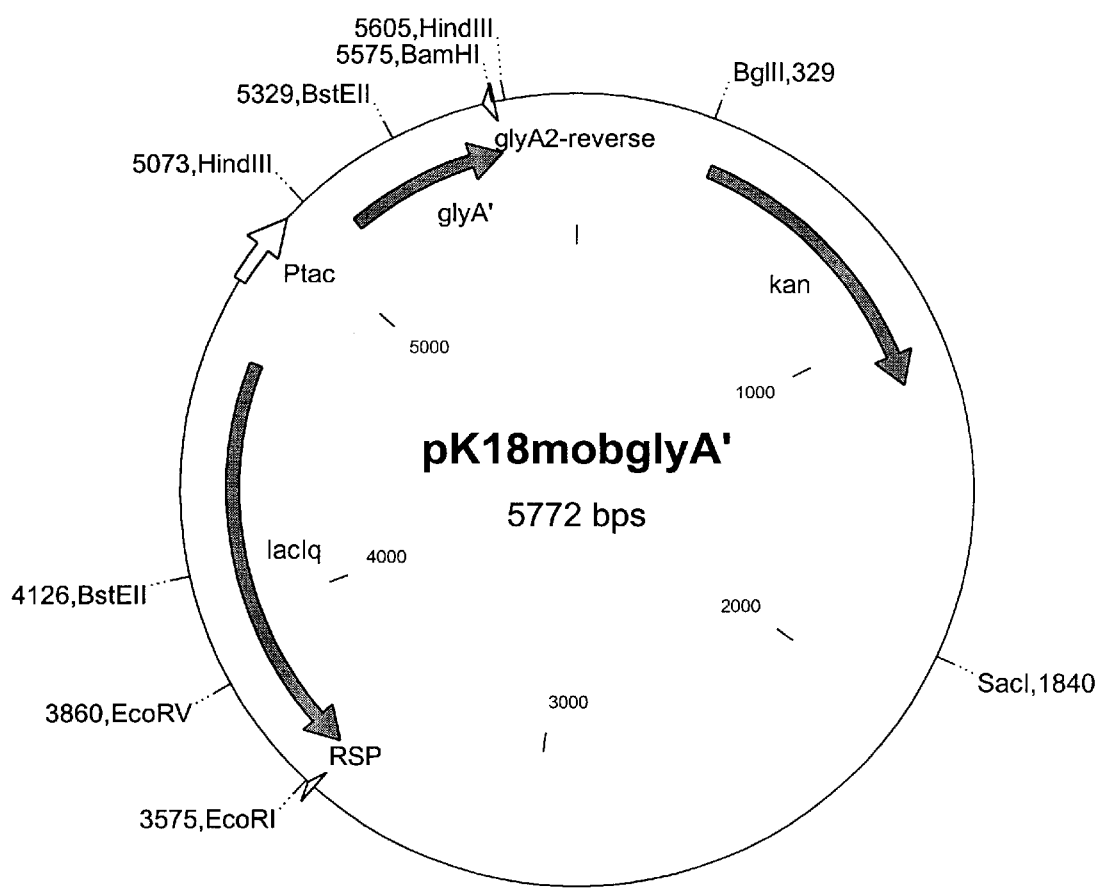

SEQUENCE LISTING

<160> NUMBER OF SEQ ID NOS: 10

<210> SEQ ID NO 1
<211> LENGTH: 438
<212> TYPE: DNA
<213> ORGANISM: Corynebacterium glutamicum
<220> FEATURE:
<221> NAME/KEY: N_region
<222> LOCATION: (1)..(438)
<223> OTHER INFORMATION: 5'gly

<400> SEQUENCE: 1

```
atgaccgatg cccaccaagc ggacgatgtc cgttaccagc cactgaacga gcttgatcct      60
gaggtggctg ctgccatcgc tggggaactt gcccgtcaac gcgatacatt agagatgatc     120
gcgtctgaga acttcgttcc ccgttctgtt ttgcaggcgc agggttctgt tcttaccaat     180
aagtatgccg agggttaccc tggccgccgt tactacggtg gttgcgaaca agttgacatc     240
attgaggatc ttgcacgtga tcgtgcgaag gctctcttcg gtgcagagtt cgccaatgtt     300
cagcctcact ctggcgcaca ggctaatgct gctgtgctga tgactttggc tgagccaggc     360
gacaagatca tgggtctgtc tttggctcat ggtggtcact tgacccacgg aatgaagttg     420
aacttctccg gaaagctg                                                    438
```

<210> SEQ ID NO 2
<211> LENGTH: 2000
<212> TYPE: DNA
<213> ORGANISM: Corynebacterium glutamicum
<220> FEATURE:
<221> NAME/KEY: gene
<222> LOCATION: (6)..(1097)
<223> OTHER INFORMATION: lacI
<221> NAME/KEY: promoter
<222> LOCATION: (1391)..(1434)
<223> OTHER INFORMATION: tac
<221> NAME/KEY: N_region
<222> LOCATION: (1562)..(1999)
<223> OTHER INFORMATION: 5'glyA

<400> SEQUENCE: 2

-continued

```
aattctcact gcccgctttc cagtcgggaa acctgtcgtg ccagctgcat taatgaatcg    60
gccaacgcgc ggggagaggc ggtttgcgta ttgggcgcca gggtggtttt tcttttcacc   120
agtgagacgg gcaacagctg attgcccttc accgcctggc cctgagagag ttgcagcaag   180
cggtccacgc tggtttgccc cagcaggcga aaatcctgtt tgatggtggt tgacggcggg   240
atataacatg agctgtcttc ggtatcgtcg tatcccacta ccgagatatc cgcaccaacg   300
cgcagcccgg actcggtaat ggcgcgcatt gcgcccagcg ccatctgatc gttggcaacc   360
agcatcgcag tgggaacgat gccctcattc agcatttgca tggtttgttg aaaaccggac   420
atggcactcc agtcgccttc ccgttccgct atcggctgaa tttgattgcg agtgagatat   480
ttatgccagc cagccagacg cagacgcgcc gagacagaac ttaatgggcc cgctaacagc   540
gcgatttgct ggtgacccaa tgcgaccaga tgctccacgc ccagtcgcgt accgtcttca   600
tgggagaaaa taatactgtt gatgggtgtc tggtcagaga catcaagaaa taacgccgga   660
acattagtgc aggcagcttc cacagcaatg gcatcctggt catccagcgg atagttaatg   720
atcagcccac tgacgcgttg cgcgagaaga ttgtgcaccg ccgctttaca ggcttcgacg   780
ccgcttcgtt ctaccatcga caccaccacg ctggcaccca gttgatcggc gcgagattta   840
atcgccgcga caatttgcga cggcgcgtgc agggccagac tggaggtggc aacgccaatc   900
agcaacgact gtttgcccgc cagttgttgt gccacgcggt tgggaatgta attcagctcc   960
gccatcgccg cttccacttt ttcccgcgtt ttcgcagaaa cgtggctggc ctggttcacc  1020
acgcgggaaa cggtctgata agagacaccg gcatactctg cgacatcgta taacgttact  1080
ggtttcacat tcaccaccct gaattgactc tcttccgggc gctatcatgc cataccgcga  1140
aaggttttgc accattcgat ggtgtcaacg taaatgcatg ccgcttcgcc ttcgcgcgcg  1200
aattgcaagc tgatccgggc ttatcgactg cacggtgcac caatgcttct ggcgtcaggc  1260
agccatcgga agctgtggta tggctgtgca ggtcgtaaat cactgcataa ttcgtgtcgc  1320
tcaaggcgca ctcccgttct ggataatgtt ttttgcgccg acatcataac ggttctggca  1380
aatattctga aatgagctgt tgacaattaa tcatcggctc gtataatgtg tggaattgtg  1440
agcggataac aatttcacac aggaaacaga attaaaagat atgaccatga ttacgccaag  1500
cttgcatgcc tgcaggtcga ctctagagga tcattcgtct tgtgaaaggt tagctgacct  1560
gatgaccgat gcccaccaag cggacgatgt ccgttaccag ccactgaacg agcttgatcc  1620
tgaggtggct gctgccatcg ctgggaact tgcccgtcaa cgcgatacat tagagatgat  1680
cgcgtctgag aacttcgttc cccgttctgt tttgcaggcg cagggttctg ttcttaccaa  1740
taagtatgcc gagggttacc ctggccgccg ttactacggt ggttgcgaac aagttgacat  1800
cattgaggat cttgcacgtg atcgtgcgaa ggctctcttc ggtgcagagt tcgccaatgt  1860
tcagcctcac tctggcgcac aggctaatgc tgctgtgctg atgactttgg ctgagccagg  1920
cgacaagatc atgggtctgt ctttggctca tggtggtcac ttgacccacg gaatgaagtt  1980
gaacttctcc ggaaagctgg                                             2000
```

<210> SEQ ID NO 3
<211> LENGTH: 2866
<212> TYPE: DNA
<213> ORGANISM: Corynebacterium glutamicum
<220> FEATURE:
<221> NAME/KEY: gene
<222> LOCATION: (6)..(1097)
<223> OTHER INFORMATION: lacI
<221> NAME/KEY: promoter

```
<222> LOCATION: (1391)..(1434)
<223> OTHER INFORMATION: tac
<221> NAME/KEY: CDS
<222> LOCATION: (1562)..(2863)
<223> OTHER INFORMATION: glyA

<400> SEQUENCE: 3
```

| | |
|---|---:|
| aattctcact gcccgctttc cagtcgggaa acctgtcgtg ccagctgcat taatgaatcg | 60 |
| gccaacgcgc ggggagaggc ggtttgcgta ttgggcgcca gggtggtttt tcttttcacc | 120 |
| agtgagacgg gcaacagctg attgcccttc accgcctggc cctgagagag ttgcagcaag | 180 |
| cggtccacgc tggtttgccc cagcaggcga aaatcctgtt tgatggtggt tgacggcggg | 240 |
| atataacatg agctgtcttc ggtatcgtcg tatcccacta ccgagatatc cgcaccaacg | 300 |
| cgcagcccgg actcggtaat ggcgcgcatt gcgcccagcg ccatctgatc gttggcaacc | 360 |
| agcatcgcag tgggaacgat gccctcattc agcatttgca tggtttgttg aaaaccggac | 420 |
| atggcactcc agtcgccttc ccgttccgct atcggctgaa tttgattgcg agtgagatat | 480 |
| ttatgccagc cagccagacg cagacgcgcc gagacagaac ttaatgggcc cgctaacagc | 540 |
| gcgatttgct ggtgacccaa tgcgaccaga tgctccacgc ccagtcgcgt accgtcttca | 600 |
| tgggagaaaa taatactgtt gatgggtgtc tggtcagaga catcaagaaa taacgccgga | 660 |
| acattagtgc aggcagcttc cacagcaatg gcatcctggt catccagcgg atagttaatg | 720 |
| atcagcccac tgacgcgttg cgcgagaaga ttgtgcaccg ccgctttaca ggcttcgacg | 780 |
| ccgcttcgtt ctaccatcga caccaccacg ctggcaccca gttgatcggc gcgagattta | 840 |
| atcgccgcga caatttgcga cggcgcgtgc agggccagac tggaggtggc aacgccaatc | 900 |
| agcaacgact gtttgcccgc cagttgttgt gccacgcggt tgggaatgta attcagctcc | 960 |
| gccatcgccg cttccacttt ttcccgcgtt ttcgcagaaa cgtggctggc ctggttcacc | 1020 |
| acgcgggaaa cggtctgata agagacaccg gcatactctg cgacatcgta taacgttact | 1080 |
| ggtttcacat tcaccaccct gaattgactc tcttccgggc gctatcatgc cataccgcga | 1140 |
| aaggttttgc accattcgat ggtgtcaacg taaatgcatg ccgcttcgcc ttcgcgcgcg | 1200 |
| aattgcaagc tgatccgggc ttatcgactg cacggtgcac caatgcttct ggcgtcaggc | 1260 |
| agccatcgga agctgtggta tggctgtgca ggtcgtaaat cactgcataa ttcgtgtcgc | 1320 |
| tcaaggcgca ctcccgttct ggataatgtt ttttgcgccg acatcataac ggttctggca | 1380 |
| aatattctga aatgagctgt tgacaattaa tcatcggctc gtataatgtg tggaattgtg | 1440 |
| agcggataac aatttcacac aggaaacaga attaaagat atgaccatga ttacgccaag | 1500 |
| cttgcatgcc tgcaggtcga ctctagagga tcattcgtct tgtgaaaggt tagctgacct | 1560 |

| | | |
|---|---|---:|
| g atg acc gat gcc cac caa gcg gac gat gtc cgt tac cag cca ctg aac | | 1609 |
|   Met Thr Asp Ala His Gln Ala Asp Asp Val Arg Tyr Gln Pro Leu Asn | | |
|    1               5              10             15 | | |
| gag ctt gat cct gag gtg gct gct gcc atc gct ggg gaa ctt gcc cgt | | 1657 |
| Glu Leu Asp Pro Glu Val Ala Ala Ala Ile Ala Gly Glu Leu Ala Arg | | |
|           20              25             30 | | |
| caa cgc gat aca tta gag atg atc gcg tct gag aac ttc gtt ccc cgt | | 1705 |
| Gln Arg Asp Thr Leu Glu Met Ile Ala Ser Glu Asn Phe Val Pro Arg | | |
|           35              40             45 | | |
| tct gtt ttg cag gcg cag ggt tct gtt ctt acc aat aag tat gcc gag | | 1753 |
| Ser Val Leu Gln Ala Gln Gly Ser Val Leu Thr Asn Lys Tyr Ala Glu | | |
|           50              55             60 | | |
| ggt tac cct ggc cgc cgt tac tac ggt ggt tgc gaa caa gtt gac atc | | 1801 |
| Gly Tyr Pro Gly Arg Arg Tyr Tyr Gly Gly Cys Glu Gln Val Asp Ile | | |
| 65                 70             75             80 | | |

```
att gag gat ctt gca cgt gat cgt gcg aag gct ctc ttc ggt gca gag     1849
Ile Glu Asp Leu Ala Arg Asp Arg Ala Lys Ala Leu Phe Gly Ala Glu
             85                  90                  95 ttc gcc aat gtt cag cct cac tct ggc gca cag gct aat gct gct gtg     1897
Phe Ala Asn Val Gln Pro His Ser Gly Ala Gln Ala Asn Ala Ala Val
            100                 105                 110 ctg atg act ttg gct gag cca ggc gac aag atc atg ggt ctg tct ttg     1945
Leu Met Thr Leu Ala Glu Pro Gly Asp Lys Ile Met Gly Leu Ser Leu
            115                 120                 125 gct cat ggt ggt cac ttg acc cac gga atg aag ttg aac ttc tcc gga     1993
Ala His Gly Gly His Leu Thr His Gly Met Lys Leu Asn Phe Ser Gly
        130                 135                 140 aag ctg tac gag gtt gtt gcg tac ggt gtt gat cct gag acc atg cgt     2041
Lys Leu Tyr Glu Val Val Ala Tyr Gly Val Asp Pro Glu Thr Met Arg
145                 150                 155                 160 gtt gat atg gat cag gtt cgt gag att gct ctg aag gag cag cca aag     2089
Val Asp Met Asp Gln Val Arg Glu Ile Ala Leu Lys Glu Gln Pro Lys
                165                 170                 175 gta att atc gct ggc tgg tct gca tac cct cgc cac ctt gat ttc gag     2137
Val Ile Ile Ala Gly Trp Ser Ala Tyr Pro Arg His Leu Asp Phe Glu
            180                 185                 190 gct ttc cag tct att gct gcg gaa gtt ggc gcg aag ctg tgg gtc gat     2185
Ala Phe Gln Ser Ile Ala Ala Glu Val Gly Ala Lys Leu Trp Val Asp
            195                 200                 205 atg gct cac ttc gct ggt ctt gtt gct gct ggt ttg cac cca agc cca     2233
Met Ala His Phe Ala Gly Leu Val Ala Ala Gly Leu His Pro Ser Pro
        210                 215                 220 gtt cct tac tct gat gtt gtt tct tcc act gtc cac aag act ttg ggt     2281
Val Pro Tyr Ser Asp Val Val Ser Ser Thr Val His Lys Thr Leu Gly
225                 230                 235                 240 gga cct cgt tcc ggc atc att ctg gct aag cag gag tac gcg aag aag     2329
Gly Pro Arg Ser Gly Ile Ile Leu Ala Lys Gln Glu Tyr Ala Lys Lys
                245                 250                 255 ctg aac tct tcc gta ttc cca ggt cag cag ggt ggt cct ttg atg cac     2377
Leu Asn Ser Ser Val Phe Pro Gly Gln Gln Gly Gly Pro Leu Met His
            260                 265                 270 gca gtt gct gcg aag gct act tct ttg aag att gct ggc act gag cag     2425
Ala Val Ala Ala Lys Ala Thr Ser Leu Lys Ile Ala Gly Thr Glu Gln
        275                 280                 285 ttc cgt gac cgt cag gct cgc acg ttg gag ggt gct cgc att ctt gct     2473
Phe Arg Asp Arg Gln Ala Arg Thr Leu Glu Gly Ala Arg Ile Leu Ala
        290                 295                 300 gag cgt ctg act gct tct gat gcg aag gcc gct ggc gtg gat gtc ttg     2521
Glu Arg Leu Thr Ala Ser Asp Ala Lys Ala Ala Gly Val Asp Val Leu
305                 310                 315                 320 acc ggt ggc act gat gtg cac ttg gtt ttg gct gat ctg cgt aac tcc     2569
Thr Gly Gly Thr Asp Val His Leu Val Leu Ala Asp Leu Arg Asn Ser
                325                 330                 335 cag atg gat ggc cag cag gcg gaa gat ctg ctg cac gag gtt ggt atc     2617
Gln Met Asp Gly Gln Gln Ala Glu Asp Leu Leu His Glu Val Gly Ile
            340                 345                 350 act gtg aac cgt aac gcg gtt cct ttc gat cct cgt cca cca atg gtt     2665
Thr Val Asn Arg Asn Ala Val Pro Phe Asp Pro Arg Pro Pro Met Val
            355                 360                 365 act tct ggt ctg cgt att ggt act cct gcg ctg gct acc cgt ggt ttc     2713
Thr Ser Gly Leu Arg Ile Gly Thr Pro Ala Leu Ala Thr Arg Gly Phe
        370                 375                 380 gat att cct gca ttc act gag gtt gca gac atc att ggt act gct ttg     2761
Asp Ile Pro Ala Phe Thr Glu Val Ala Asp Ile Ile Gly Thr Ala Leu
```

```
                385                 390                 395                 400
gct aat ggt aag tcc gca gac att gag tct ctg cgt ggc cgt gta gca                        2809
Ala Asn Gly Lys Ser Ala Asp Ile Glu Ser Leu Arg Gly Arg Val Ala
                405                 410                 415 aag ctt gct gca gat tac cca ctg tat gag ggc ttg gaa gac tgg acc                        2857
Lys Leu Ala Ala Asp Tyr Pro Leu Tyr Glu Gly Leu Glu Asp Trp Thr
        420                 425                 430 atc gtc taa                                                                            2866
Ile Val <210> SEQ ID NO 4
<211> LENGTH: 434
<212> TYPE: PRT
<213> ORGANISM: Corynebacterium glutamicum
<220> FEATURE:
<223> OTHER INFORMATION: Description of the synthetic sequence:LacI-tac-
      glyA

<400> SEQUENCE: 4

Met Thr Asp Ala His Gln Ala Asp Val Arg Tyr Gln Pro Leu Asn
1               5                   10                  15

Glu Leu Asp Pro Glu Val Ala Ala Ile Ala Gly Glu Leu Ala Arg
            20                  25                  30

Gln Arg Asp Thr Leu Glu Met Ile Ala Ser Glu Asn Phe Val Pro Arg
        35                  40                  45

Ser Val Leu Gln Ala Gln Gly Ser Val Leu Thr Asn Lys Tyr Ala Glu
    50                  55                  60

Gly Tyr Pro Gly Arg Arg Tyr Tyr Gly Gly Cys Glu Gln Val Asp Ile
65                  70                  75                  80

Ile Glu Asp Leu Ala Arg Asp Arg Ala Lys Ala Leu Phe Gly Ala Glu
                85                  90                  95

Phe Ala Asn Val Gln Pro His Ser Gly Ala Gln Ala Asn Ala Ala Val
            100                 105                 110

Leu Met Thr Leu Ala Glu Pro Gly Asp Lys Ile Met Gly Leu Ser Leu
        115                 120                 125

Ala His Gly Gly His Leu Thr His Gly Met Lys Leu Asn Phe Ser Gly
    130                 135                 140

Lys Leu Tyr Glu Val Val Ala Tyr Gly Val Asp Pro Glu Thr Met Arg
145                 150                 155                 160

Val Asp Met Asp Gln Val Arg Glu Ile Ala Leu Lys Glu Gln Pro Lys
                165                 170                 175

Val Ile Ile Ala Gly Trp Ser Ala Tyr Pro Arg His Leu Asp Phe Glu
            180                 185                 190

Ala Phe Gln Ser Ile Ala Ala Glu Val Gly Ala Lys Leu Trp Val Asp
        195                 200                 205

Met Ala His Phe Ala Gly Leu Val Ala Ala Gly Leu His Pro Ser Pro
    210                 215                 220

Val Pro Tyr Ser Asp Val Val Ser Ser Thr Val His Lys Thr Leu Gly
225                 230                 235                 240

Gly Pro Arg Ser Gly Ile Ile Leu Ala Lys Gln Glu Tyr Ala Lys Lys
                245                 250                 255

Leu Asn Ser Ser Val Phe Pro Gly Gln Gln Gly Pro Leu Met His
            260                 265                 270

Ala Val Ala Ala Lys Ala Thr Ser Leu Lys Ile Ala Gly Thr Glu Gln
        275                 280                 285

Phe Arg Asp Arg Gln Ala Arg Thr Leu Glu Gly Ala Arg Ile Leu Ala
```

-continued

```
            290                 295                 300
Glu Arg Leu Thr Ala Ser Asp Ala Lys Ala Ala Gly Val Asp Val Leu
305                 310                 315                 320

Thr Gly Gly Thr Asp Val His Leu Val Leu Ala Asp Leu Arg Asn Ser
                325                 330                 335

Gln Met Asp Gly Gln Gln Ala Glu Asp Leu Leu His Glu Val Gly Ile
            340                 345                 350

Thr Val Asn Arg Asn Ala Val Pro Phe Asp Pro Arg Pro Met Val
            355                 360                 365

Thr Ser Gly Leu Arg Ile Gly Thr Pro Ala Leu Ala Thr Arg Gly Phe
    370                 375                 380

Asp Ile Pro Ala Phe Thr Glu Val Ala Asp Ile Ile Gly Thr Ala Leu
385                 390                 395                 400

Ala Asn Gly Lys Ser Ala Asp Ile Glu Ser Leu Arg Gly Arg Val Ala
                405                 410                 415

Lys Leu Ala Ala Asp Tyr Pro Leu Tyr Glu Gly Leu Glu Asp Trp Thr
            420                 425                 430

Ile Val
```

<210> SEQ ID NO 5
<211> LENGTH: 22
<212> TYPE: DNA
<213> ORGANISM: Corynebacterium glutamicum

<400> SEQUENCE: 5
gcttgcagcg ttttgctctg cc                                    22

<210> SEQ ID NO 6
<211> LENGTH: 23
<212> TYPE: DNA
<213> ORGANISM: Corynebacterium glutamicum

<400> SEQUENCE: 6
acccgtaacc tcttccacat agg                                   23

<210> SEQ ID NO 7
<211> LENGTH: 17
<212> TYPE: DNA
<213> ORGANISM: Corynebacterium glutamicum

<400> SEQUENCE: 7
gtaaaacgac ggccagt                                          17

<210> SEQ ID NO 8
<211> LENGTH: 19
<212> TYPE: DNA
<213> ORGANISM: Corynebacterium glutamicum

<400> SEQUENCE: 8
ggaaacagct atgaccatg                                        19

<210> SEQ ID NO 9
<211> LENGTH: 29
<212> TYPE: DNA
<213> ORGANISM: Corynebacterium glutamicum

<400> SEQUENCE: 9
ccggaattct cactgcccgc tttccagtc                             29

```
<210> SEQ ID NO 10
<211> LENGTH: 30
<212> TYPE: DNA
<213> ORGANISM: Corynebacterium glutamicum

<400> SEQUENCE: 10
cgggatccca gctttccgga gaagttcaac                              30
```

PROCESS FOR THE FERMENTATIVE PREPARATION OF L-AMINO ACIDS USING CORYNEFORM BACTERIA

INTRODUCTION AND BACKGROUND

The invention relates to a process for the fermentative preparation of L-amino acids, in particular L-threonine, using coryneform bacteria in which the glyA gene is attenuated. All references cited herein are expressly incorporated by reference. Incorporation by reference is also designated by the term "I.B.R." following a citation.

PRIOR ART

L-Amino acids are used in animal nutrition, in human medicine and in the pharmaceuticals industry. It is known that amino acids are prepared by fermentation from strains of coryneform bacteria, in particular *Corynebacterium glutamicum*. Because of their great importance, work is constantly being undertaken to improve the preparation processes.

Improvements to the processes can relate to fermentation measures, such as, for example, stirring and supply of oxygen, or the composition of the nutrient media, such as the sugar concentration during the fermentation, or the working up to the product form by, for example, ion exchange chromatography, or the intrinsic output properties of the microorganism itself.

Methods of mutagenesis, selection and mutant selection are used to improve the output properties of these microorganisms. Strains which are resistant to antimetabolites, such as the threonine analogue α-amino-β-hydroxyvaleric acid (AHV), or are auxotrophic for metabolites of regulatory importance and produce L-amino acids such as threonine are obtained in this manner.

Recombinant DNA techniques have also been employed for some years for improving the strain of *Corynebacterium glutamicum* strains which produce L-amino acids, by amplifying individual amino acid biosynthesis genes and investigating the effect on the L-amino acid production. Review articles in this context are to be found, inter alia, in Kinoshita (Glutamic Acid Bacteria, in: Biology of Industrial Microorganisms, Demain and Solomon (Eds.), Benjamin Cummings, London, UK, 1985, 115–142) I.B.R., Hilliger (BioTec 2, 40–44 (1991)) I.B.R., Eggeling (Amino Acids 6, 261–272 (1994)) I.B.R., Jetten and Sinskey (Critical Reviews in Biotechnology 15, 73–103 (1995)) I.B.R. and Sahm et al. (Annuals of the New York Academy of Science 782, 25–39 (1996)) I.B.R.

OBJECT OF THE INVENTION

An object of this invention is to provide new and improved processes for the fermentative preparation of L-amino acids with coryneform bacteria. L-Amino acids are used in human medicine and in the pharmaceuticals industry, in the foodstuffs industry and especially in animal nutrition. There is therefore a general interest in providing new improved processes for the preparation of amino acids. Where L-amino acid is mentioned below, this means L-threonine or L-isoleucine.

SUMMARY OF THE INVENTION

The invention provides a process for the fermentative preparation of L-amino acids using coryneform bacteria in which at least the nucleotide sequence which codes for the glyA gene product (glyA gene) is attenuated, and in particular expressed at a low level. The desired product is concentrated in the medium or in the cells and the L-amino acid is isolated. The strains employed preferably already produce L-amino acids before attenuation of the glyA gene.

BRIEF DESCRIPTION OF THE DRAWINGS

FIG. 1: Map of the plasmid pK18mobglyA'. The length data are to be understood as approx. values.

DETAILED DESCRIPTION OF THE INVENTION

The term "attenuation" in this connection describes the reduction or elimination of the intracellular activity of one or more enzymes (proteins) in a microorganism which are coded by the corresponding DNA (here the glyA gene). For example, this can be accomplished by using a weak promoter or using a gene or an allele which codes for a corresponding enzyme with a low activity or inactivates the corresponding gene or enzyme (protein), and optionally combining these measures.

The microorganisms to which the present invention relates can prepare amino acids from glucose, sucrose, lactose, fructose, maltose, molasses, starch, cellulose or from glycerol and ethanol. They can be representatives of coryneform bacteria, in particular of the genus Corynebacterium. Of the genus Corynebacterium, there may be mentioned in particular the species *Corynebacterium glutamicum*, which is known among experts for its ability to produce L-amino acids.

Suitable strains of the genus Corynebacterium, in particular of the species *Corynebacterium glutamicum*, are in particular the known wild-type strains

*Corynebacterium glutamicum* ATCC13032
*Corynebacterium acetoglutamicum* ATCC15806
*Corynebacterium acetoacidophilum* ATCC13870
*Corynebacterium melassecola* ATCC17965
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020 and L-amino acid-producing mutants or strains prepared therefrom such as, for example, the L-threonine-producing strains

*Corynebacterium glutamicum* ATCC21649
*Brevibacterium flavum* BB69
*Brevibacterium flavum* DSM5399
*Brevibacterium lactofermentum* FERM-BP 269
*Brevibacterium lactofermentum* TBB-10 and such as, for example, the L-isoleucine-producing strains

*Corynebacterium glutamicum* ATCC 14309
*Corynebacterium glutamicum* ATCC 14310
*Corynebacterium glutamicum* ATCC 14311
*Corynebacterium glutamicum* ATCC 15168
*Corynebacterium ammoniagenes* ATCC 6871.

It has been found that coryneform bacteria produce L-amino acids in an improved manner after attenuation of the glyA gene. The glyA gene codes for the enzyme serine hydroxymethyltransferase (EC 2.1.2.1) I.B.R. The nucleotide sequence of the glyA gene has been described in Japanese Laid-Open Specification JP-A-08107788 I.B.R. The glyA gene described in the text reference mentioned can be used according to the invention. Alleles of the glyA gene which result from the degeneracy of the genetic code or due to sense mutations of neutral function can furthermore be used.

To achieve an attenuation, either the expression of the glyA gene or the catalytic properties of the gene product can be reduced or eliminated. The two measures are optionally combined.

The gene expression can be reduced by suitable culturing or by genetic modification (mutation) of the signal structures of gene expression. Signal structures of gene expression are, for example, repressor genes, activator genes, operators, promoters, attenuators, ribosome binding sites, the start codon and terminators.

The expert can find information on this e.g. in the patent application WO 96/15246 I.B.R., in Boyd and Murphy (Journal of Bacteriology 170: 5949 (1988)) I.B.R., in Voskuil and Chambliss (Nucleic Acids Research 26: 3548 (1998) I.B.R., in Jensen and Hammer (Biotechnology and Bioengineering 58: 191 (1998)) I.B.R., in Pátek et al. (Microbiology 142: 1297 (1996)) I.B.R. and in known textbooks of genetics and molecular biology, such as e.g. the textbook by Knippers ("Molekulare Genetik" [Molecular Genetics], 6th edition, Georg Thieme Verlag, Stuttgart, Germany, 1995) I.B.R. or that by Winnacker ("Gene und Klone" [Genes and Clones], VCH Verlagsgesellschaft, Weinheim, Germany, 1990) I.B.R.

Mutations which lead to a change or reduction in the catalytic properties of enzyme proteins are known from the prior art; examples which may be mentioned are the works by Qiu and Goodman (Journal of Biological Chemistry 272: 8611–8617 (1997)) I.B.R., Sugimoto et al. (Bioscience Biotechnology and Biochemistry 61: 1760–1762 (1997)) I.B.R. and Möckel ("Die Threonindehydratase aus Corynebacterium glutamicum: Aufhebung der allosterischen Regulation und Struktur des Enzyms" [Threonine dehydratase from Corynebacterium glutamicum: Cancelling the allosteric regulation and structure of the enzyme], Reports from the Jülich Research Centre, Jül-2906, ISSN09442952, J ülich, Germany, 1994) I.B.R.

The relative degree of substitution or mutation in the polynucleotide or amino acid sequence to produce a desired percentage of sequence identity can be established or determined by well-known methods of sequence analysis. These methods are disclosed and demonstrated in Bishop, et al. "DNA & Protein Sequence Analysis (A Practical Approach"), Oxford Univ. Press, Inc. (1997) I.B.R. and by Steinberg, Michael "Protein Structure Prediction" (A Practical Approach), Oxford Univ. Press, Inc. (1997) I.B.R.

Hybridization of complementary sequences can occur at varying degrees of stringency. Sambrook et al.: Molecular Cloning, A Laboratory Manual (Cold Spring Harbor Laboratory Press, 1989) I.B.R. Instructions for identifying DNA sequences by means of hybridization can be found by the expert, inter alia, in the handbook "The DIG System Users Guide for Filter Hybridization" from Boehringer Mannheim GmbH (Mannheim, Germany, 1993)I.B.R. and in Liebl et al. (International Journal of Systematic Bacteriology (1991) 41: 255–260)I.B.R.

Comprehensive descriptions can be found in known textbooks of genetics and molecular biology, such as e.g. that by Hagemann ("Allgemeine Genetik" [General Genetics], Gustav Fischer Verlag, Stuttgart, 1986) I.B.R.

Possible mutations are transitions, transversions, insertions and deletions. Depending on the effect of the amino acid exchange on the enzyme activity, missense mutations or nonsense mutations are referred to. Insertions or deletions of at least one base pair in a gene lead to frame shift mutations, as a consequence of which incorrect amino acids are incorporated or translation is interrupted prematurely. Deletions of several codons typically lead to a complete loss of the enzyme activity.

Instructions on generation of such mutations are prior art and can be found in known textbooks of genetics and molecular biology, such as e.g. the textbook by Knippers ("Molekulare Genetik" [Molecular Genetics], 6th edition, Georg Thieme Verlag, Stuttgart, Germany, 1995) I.B.R., that by Winnacker ("Gene und Klone" [Genes and Clones], VCH Verlagsgesellschaft, Weinheim, Germany, 1990) I.B.R. or that by Hagemann ("Allgemeine Genetik" [General Genetics], Gustav Fischer Verlag, Stuttgart, 1986) I.B.R.

By way of example, the glyA gene was attenuated by removal of the natural promoter and insertion of a regulatable control element lying upstream. The lacI-tac system was used as the control element. To be able to achieve incorporation of the lacI-tac system upstream of the chromosomal glyA gene, the integration plasmid pK18mobglyA' (FIG. 1) was prepared.

The plasmid pK18mobglyA' contains the tac promoter (Amann et al., Gene 25: 167–178 (1983) I.B.R.; De Boer et al., Proceedings of the National Academy of Sciences of the United States of America USA 80: 21–25 (1983)) I.B.R. and directly downstream of the tac promoter a 5'-terminal sequence of the glyA gene shown in SEQ ID No 1. The plasmid furthermore contains the lacI gene which codes for the Lac inhibitor (Farabaugh, Nature 274: 765–769 (1978); Stark et al., Gene 51: 255–267 (1987)) I.B.R.

The sequence of the lacI-tac-5'glyA unit is shown in SEQ ID No 2. Plasmid pK18mobglyA' is capable of replication in Escherichia coli but not in Corynebacterium glutamicum. After transformation and homologous recombination by means of a "cross-over" event which effects integration, an intact copy of the glyA gene, expression of which can be controlled or regulated by the lacI-tac control element lying upstream, and an inactive copy of the glyA gene truncated on the 3'-terminus, including the natural promoter, are obtained.

The sequence of the lacI-tac-glyA unit is shown in SEQ ID No 3. SEQ ID No 4 shows the known amino acid sequence of the glyA gene product. By addition of suitable concentrations of the lactose analogue isopropyl thiogalactoside (Fürste et al., Gene 48: 119–131 (1986)) I.B.R., the expression of the glyA gene can be controlled or the cell content of serine hydroxymethyltransferase can be attenuated or adjusted.

Further instructions and explanations on integration mutagenesis are to be found, for example, in Schwarzer and Pühler (Bio/Technology 9,84–87 (1991)) I.B.R., Peters-Wendisch et al. (Microbiology 144, 915–927 (1998)) I.B.R. or Fitzpatrick et al. (Applied Microbiology Biotechnology 42, 575–580 (1994)) I.B.R.

An example of an amino acid-producing strain of coryneform bacteria with an attenuated glyA gene is the threonine producer Corynebacterium glutamicum DM368–2::pK18mobglyA'.

In addition, it may be advantageous for the production of amino acids to amplify one or more enzymes of the particular biosynthesis pathway, of glycolysis, of anaplerosis, of the citric acid cycle or of amino acid export, in addition to attenuation of the glyA gene.

Thus, for example, for the preparation of L-threonine
at the same time the hom gene which codes for
homoserine dehydrogenase (Peoples et al., Molecular
Microbiology 2, 63–72 (1988)) I.B.R. or the $hom^{dr}$ allele which codes for a "feed back resistant" homoserine dehydrogenase (Archer et al., Gene 107, 53–59 (1991)) I.B.R. and/or at the same time the gap gene which codes for glyceraldehyde 3-phosphate dehydrogenase (Eikmanns et al., Journal of Bacteriology 174: 6076–6086 (1992)) I.B.R., or at the same time the pyc gene which codes for pyruvate carboxylase (Peters-Wendisch et al., Microbiology 144: 915–927 (1998)) I.B.R., or at the same time the mqo gene which codes for malate-:quinone oxidoreductase (Molenaar et al., European Journal of Biochemistry 254, 395–403 (1998)) I.B.R., or at the same time the thrE gene which codes for threonine export (DE 199 41 478.5; DSM 12840) I.B.R.

can be over-expressed.

For the production of amino acids it may furthermore be advantageous to attenuate, in addition to the glyA gene, the pck gene which codes for phosphoenol pyruvate carboxykinase (DE 199 50 409.1; DSM 13047) I.B.R. and/or the poxB gene which codes for pyruvate oxidase (DE 199 51 975.7; DSM 13114) I.B.R.

at the same time.

Finally, in addition to attenuation of the glyA gene it may be advantageous for the production of amino acids to eliminate undesirable side reactions (Nakayama: "Breeding of Amino Acid Producing Microorganisms", in: Overproduction of Microbial Products, Krumphanzl, Sikyta, Vanek (eds.), Academic Press, London, UK, 1982) I.B.R.

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981) I.B.R. Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substance can be used individually or as a mixture.

Organic nitrogen-containing compounds, such as peptones, yeast extract, meat extract, malt extract, corn steep liquor, soya bean flour and urea, or inorganic compounds, such as ammonium sulphate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as e.g. magnesium sulfate or iron sulfate, which are necessary for growth. Finally, essential growth substances, such as amino acids and vitamins, can be employed in addition to the above-mentioned substances.

Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH. Antifoams, such as e.g. fatty acid polyglycol esters, can be employed to control the development of foam. Suitable substances having a selective action, such as e.g. antibiotics, can be added to the medium to maintain the stability of plasmids.

To maintain aerobic conditions, oxygen or oxygen-containing gas mixtures, such as e.g. air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

Methods for the determination of L-amino acids are known from the prior art. The analysis can thus be carried out as described by Spackman et al. (Analytical Chemistry, 30, (1958), 1190) I.B.R. by anion exchange chromatography with subsequent ninhydrin derivatization, or it can be carried out by reversed phase HPLC, for example as described by Lindroth et al. (Analytical Chemistry (1979) 51: 1167–1174) I.B.R.

The following microorganism has been deposited at the Deutsche Sammlung für Mikrorganismen und Zellkulturen (DSMZ =German Collection of Microorganisms and Cell Cultures, Braunschweig, Germany) in accordance with the Budapest Treaty:

Escherichia coli strain DH5α mcr/pK18mobglyA' as DSM 13170

EXAMPLES

The present invention is explained in more detail in the following with the aid of embodiment examples.

The isolation of plasmid DNA from *Escherichia coli* and all techniques of restriction, Klenow and alkaline phosphatase treatment were carried out by the method of Sambrook et al. (Molecular cloning. A laboratory manual (1989) Cold Spring Harbour Laboratory Press) I.B.R. The transformation of *Escherichia coli* was carried out by the method of Chung et al. (Proceedings of the National Academy of Sciences of the United States of America USA (1989) 86: 2172–2175) I.B.R., unless described otherwise.

Example 1

Cloning and Sequencing of the glyA Gene from *Corynebacterium glutamicum* ATCC13032

The glyA gene was cloned in the *E. coli* cloning vector pUC 18 (Norrander et al., Gene (1983) 26: 101–106, Roche Diagnostics, Mannheim, Germany) I.B.R. The cloning was carried out two steps. The gene from *Corynebacterium glutamicum* ATCC 13032 was first amplified by a polymerase chain reaction (PCR) by means of the following oligonucleotide primers derived from Japanese Laid-Open Specification JP-A-08107788 I.B.R.

```
glyA1-forward:                         SEQ ID NO: 5
5'-GCT TGC AGC GTT TTG CTC TGC C-3' glyA1-reverse:
5'-ACC CGT AAC CTC TTC CAC ATA GG-3'   SEQ ID NO: 6
```

The PCR reaction was carried out in 30 cycles in the presence of 200 µM deoxynucleotide triphosphates (dATP, dCTP, dGTP, dTTP), in each case 1 µM of the corresponding oligonucleotide, 100 ng chromosomal DNA from *Corynebacterium glutamicum* ATCC13032, 1/10 volume 10-fold reaction buffer and 2.6 units of a heat-stable Taq-/Pwo-DNA polymerase mixture (Expand High Fidelity PCR System from Roche Diagnostics, Mannheim, Germany) in a Thermocycler (PTC-100, MJ Research, Inc., Watertown, USA) under the following conditions: 94° C. for 30 seconds, 64° C. for 1 minute and 68° C. for 3 minutes.

The amplified fragment about 1.7 kb in size was then subsequently ligated with the aid of the SureClone Ligation Kit (Amersham Pharmacia Biotech, Uppsala, Sweden) into the SmaI cleavage site of the vector pUC18 in accordance with the manufacturer's instructions. The E. coli strain DH5αmcr (Grant et al., Proceedings of the National Academy of Sciences of the United States of America USA (1990) 87: 4645–4649) I.B.R. was transformed with the entire ligation batch. Transformants were identified with the aid of their carbenicillin resistance on LB-agar plates containing 50 μg/mL carbenicillin.

The plasmids were prepared from 7 of the transformants and checked for the presence of the 1.7 kb PCR fragment as an insert by restriction analysis. The recombinant plasmid formed in this way is called pUC18glyA in the following.

The nucleotide sequence of the 1.7 kb PCR fragment in plasmid pUC18glyA was determined by the dideoxy chain termination method of Sanger et al. (Proceedings of the National Academy of Sciences of the United States of America USA (1977) 74: 5463–5467) I.B.R. For this, the complete insert of pUC18glyA was sequenced with the aid of the following primers.

Universal primer:  5'-GTA AAA CGA CGG CCA GT-3'
                   SEQ ID NO: 7

Reverse primer:    5'-GGA AAC AGC TAT GAC CAT G-3'
                   SEQ ID NO: 8

The nucleotide sequences obtained were analysed with the Lasergene program package (Biocomputing Software for Windows, DNASTAR, Madison, USA) I.B.R. The result of the analysis was identification of an open reading frame of 1302 bp in length. The corresponding gene was called the glyA gene. The associated gene product comprises 434 amino acids and is reproduced as SEQ ID No 4.

Example 2

Construction of a Vector for Reduced Expression of glyA

A DNA fragment 1418 bp in size which contains the glyA gene without its own promoter region was cut out of the plasmid pUC18glyA described under example 1 with the restriction enzymes EcoRI and TfiI. The 5' and 3' ends of this fragment were treated with Klenow enzyme.

The resulting DNA fragment was ligated in the vector pVWEx2, previously linearized with BamHI, treated with Klenow enzyme and dephosphorylated (Wendisch, "Physiologische und NMR-spektroskopische Untersuchungen zur in vivo-Aktivität zentraler Stoffwechselwege im Wildstamm und in rekombinanten Stämmen von Corynebacterium glutamicum" [Physiological and NMR-spectroscopic analyses of the in vivo activity of central metabolic pathways in the wild-type strain and in recombinant strains of Corynebacterium glutamicum], Reports from the Jülich Research Centre, Jül-3397, ISSN09442952, Jülich, Germany, 1997) I.B.R., such that the glyA gene lies in the same orientation directly after the tac promoter of the vector which can be induced with isopropyl β-D-thiogalactoside (IPTG).

The E. coli strain DH5αmcr (Grant et al., Proceedings of the National Academy of Sciences of the United States of America USA (1990) 87: 4645–4649) I.B.R. was transformed with the entire ligation batch. Transformants were identified with the aid of their tetracycline resistance on LB-agar plates containing 15 μg/mL tetracycline. The plasmids were prepared from 12 transformants and checked for the presence of the 1418 bp fragment as an insert in the correct orientation with respect to the tac promoter by restriction analysis. The recombinant plasmid formed in this manner is called pVWEx2glyA in the following.

A DNA fragment which contains lacI, the gene for the repressor of the tac promoter, the tac promoter and the first 438 bp of the cloned glyA gene of corynebacterium glutamicum was then amplified from the plasmid pVWEx2glyA by a polymerase chain reaction (PCR) by means of the following oligonucleotide primers.

glyA2-forward (with the attached EcoRI recognition sequence identified by underlining):

SEQ ID NO: 9
5'-CCG GAA TTC TCA CTG CCC GCT TTC CAG TC-3'

SEQ ID NO: 10
5'-CGG GAT CCC AGC TTT CCG GAG AAG TTC AAC-3'

The PCR reaction was carried out in 30 cycles in the presence of 200 μM deoxynucleotide triphosphates (DATP, dCTP, dGTP, dTTP), in each case 1 μM of the corresponding oligonucleotide, 100 ng plasmid DNA of pVWEx2glyA, 1/10 volume of 10-fold reaction buffer and 2.6 units of a heat-stable Taq-/Pwo-DNA polymerase mixture (Expand High Fidelity PCR System from Roche Diagnostics, Mannheim, Germany) in a Thermocycler (PTC-100, MJ Research, Inc., Watertown, USA) under the following conditions: 94° C. for 30 seconds, 58° C. for 30 seconds and 72° C. for 2 minutes.

The amplified fragment about 2.0 kb in size was subsequently digested with EcoRI and BamHI, isolated with the aid of the NucleoSpin Extract 2 in 1 Kit from Macherey-Nagel (Düren, Germany) in accordance with the manufacturer's instructions and then ligated in the vector pK18mob, which had also been cleaved with EcoRI and BamHI and dephosphorylated (Schafer et al., Gene (1994) 145: 69–73) I.B.R. The E. coli strain DH5αmcr (Grant et al., Proceedings of the National Academy of Sciences of the United States of America USA (1990) 87: 4645–4649) I.B.R. was transformed with the entire ligation batch.

Transformants were identified with the aid of their kanamycin resistance on LB-agar plates containing 50 μg/mL kanamycin. The plasmids were prepared from 12 of the transformants and checked for the presence of the 2.0 kb PCR fragment as an insert by restriction analysis. The recombinant plasmid formed in this way is called pK18mobglyA' in the following (see FIG. 1).

Example 3

Construction of the Strain Corynebacterium glutamicum ATCC13032::pK18mobglyA' with Reduced, Regulatable glyA Expression By means of electroporation (Haynes et al., FEMS Microbiology Letters (1989) 61: 329–334) I.B.R., the blank vector pZ1 (Menkel et al., Applied and Environmental Microbiology (1989) 64: 549–554) I.B.R. and the plasmid pK18mobglyA' described in example 2 were introduced into the wild-type strain *Corynebacterium glutamicum* ATCC13032 (Abe et al., Journal of General and Applied Microbiology (1967) 13: 279–301) I.B.R.

After transformation with pZ1, the transformants were identified with the aid of their kanamycin resistance on LBHIS-agar places containing 15 μg/mL kanamycin (Liebl et al., FEMS Microbiology Letters (1989) 65: 299–304) I.B.R. The plasmids were prepared from 3 of the transformants and checked for the presence of the pZ1 blank vector by restriction analysis. The control strain *Corynebacterium glutamicum* ATCC13032/pZ1 was formed in this manner.

After transformation with pK18mobglyA' the plasmid had to integrate into the chromosome of *Corynebacterium glutamicum* ATCC13032 via homologous recombination of the cloned 5' end of glyA. The kanamycin-resistant clones obtained were identified on LBHIS-agar places containing 15 μg/mL kanamycin and 1 mM isopropyl β-D-thiogalactoside (IPTG) (Liebl et al., FEMS Microbiology Letters (1989) 65: 299–304) I.B.R. Correct integration of pK18mobglyA' in the chromosome was checked in 2 resulting integration mutants by a polymerase chain reaction (PCR) by means of the following oligonucleotide primers.

```
Reverse primer (RSP):
5'-GGA AAC AGC TAT GAC CAT G-3'
SEQ ID NO: 8 glyA2-reverse:
5'-CGG GAT CCC AGC TTT CCG GAG AAG TTC AAC-3'
SEQ ID NO: 10
```

The PCR reaction was carried out in 30 cycles in the presence of 200 μM deoxynucleotide triphosphates (DATP, dCTP, dGTP, dTTP), in each case 1 μM of the corresponding oligonucleotide, 100 ng chromosomal DNA from *Corynebacterium glutamicum* ATCC13032::pK18mobglyA', 1/10 volume 10-fold reaction buffer and 2.6 units of a heat-stable Taq-/Pwo-DNA polymerase mixture (Expand High Fidelity PCR System from Roche Diagnostics, Mannheim, Germany) in a Thermocycler (PTC-100, MJ Research, Inc., Watertown, USA) under the following conditions: 94° C. for 30 seconds, 48° C. for 30 seconds and 72° C. for 2 minutes.

The strain *Corynebacterium glutamicum* ATCC13032::pK18mobglyA', in which the glyA gene is present under the control of the tac promoter which can be induced with isopropyl β-D-thiogalactoside (IPTG), was formed in this manner.

Example 4

Determination of the Serine Hydroxymethyltransferase Activity Coded by the glyA gene in the Strain *Corynebacterium glutamicum* ATCC13032::pK18mobglyA'

To obtain the crude extracts for determination of the serine hydroxymethyltransferase activity coded by glyA, the strains *C. glutamicum* ATCC13032/pZ1 and *C. glutamicum* ATCC13032::pK18mobglyA' described in example 3 were precultured in 100 mL Brain Heart Infusion-Medium (Difco Laboratories, Detroit, USA) with 25 μg kanamycin/mL and 100 μM isopropyl β-D-thiogalactoside (IPTG) for 14 hours at 30° C.

The cells were then washed once with 0.9% (w/v) sodium chloride solution and 100 mL portions of CgXII medium were inoculated with this suspension such that the $OD_{600}$ (optical density at 600 nm) was 0.5. The medium was identical to the medium described by Keilhauer et al. (Journal of Bacteriology (1993) 175: 5593–5603) I.B.R., but additionally comprised 25 μg kanamycin/mL and 0, 10 or 100 μ-M isopropyl β-D-thiogalactoside (IPTG). The composition of the medium described by Keilhauer et al. is shown in table 1.

TABLE 1

Composition of medium CGXII

| Component | Concentration |
|---|---|
| $(NH_4)_2SO_4$ | 20 g/L |
| Urea | 5 g/L |
| $KH_2PO_4$ | 1 g/L |
| $K_2HPO_4$ | 1 g/L |
| $MgSO_4 \times 7\ H_2O$ | 0.25 g/L |
| 3-Morpholinopropanesulfonic acid | 42 g/L |
| $CaCl_2$ | 10 mg/L |
| $FeSO_4 \times 7\ H_2O$ | 10 mg/L |
| $MnSO_4 \times H_2O$ | 10 mg/L |
| $ZnSO_4 \times 7\ H_2O$ | 1 mg/L |
| $CuSO_4$ | 0.2 mg/L |
| $NiCl_2 \times 6\ H_2O$ | 0.02 mg/L |
| Biotin | 0.2 mg/L |
| Glucose | 40 g/L |
| Protocatechuic acid | 30 mg/L |

Culturing of the two strains was carried out at 30° C. After 10 hours, the cells were washed once with 50 mM 4-(2-hydroxyethyl)-1-piperazinethanesulfonic acid/sodium hydroxide buffer (pH 7.0) gewaschen, centrifuged off (10 minutes at 5000 revolutions per minute with a Minifuge RF from Heraeus, Osterode, Germany) and resuspended in 200 mM 4-(2-hydroxyethyl)-1-piperazinethanesulfonic acid/sodium hydroxide buffer (pH 7.0) such that the final volume was 5 mL. 50 μL 2 mM pyridoxal 5-phosphate solution and 50 μL 100 mM dithiothreitol solution were added to this cell suspension and the cells were broken down.

The cells were broken down at 0° C. by an ultrasonic disintegrator (Branson Sonifier W-250, Branson Sonic Power Co, Danbury, USA; ultrasonic exposure time 6 minutes, pulse length 100%, ultrasonic intensity 2.5). After the ultrasonic treatment, the cell debris was separated off by centrifugation (30 minutes at 4° C. and 13000 revolutions per minute in a coolable Sigma 202 MK centrifuge from Sigma-Aldrich, Deisenhofen, Germany). The supernatant was employed directly as the cell-free crude extract for determination of the enzyme activity.

The protein determination in the cell-free crude extracts was carried out photometrically by the method of Bensadoun and Weinstein (Analytical Biochemistry (1976) 70: 241–250) I.B.R. The protein content was determined here via a calibration curve plotted with bovine serum albumin as the standard.

To determine the activity of the serine hydroxymethyltransferase in the cell-free crude extracts, a discontinuous enzyme test in which the glycine form from the substrate threonine was quantified was used. The reaction batches were incubated in the following composition (modified according to Scrimgeour and Huennekens, Methods in Enzymology (1962) Vol. V: 838–843, Academic Press) I.B.R. for 15 minutens at 37° C. inkubiert: 20 mM threonine, 200 μM pyridoxal 5-phosphate, 900 μM tetrahydrofolate, 100 mM 4-(2-hydroxyethyl)-1-piperazinethanesulfonic acid/sodium hydroxide buffer (pH 7.0) and 1.0–1.5 mg protein (from the crude extract) in a final volume of 1 mL.

The reaction was stopped by addition of 0.25 volume 25% (w/v) trichloroacetic acid solution, the batches were incubated for 15 minutes at 0° C. and the denatured protein was centrifuged off (15 minutes at 4° C. and 13000 revolutions per minute in a coolable Sigma 202 MK centrifuge from Sigma-Aldrich, Deisenhofen, Germany). The quantitative determination of the glycine formed in the enzyme test from the supernatant was carried out by means of reversed phase HPLC (Lindroth et al., Analytical Chemistry (1979) 51: 1167–1174) I.B.R. An HPLC apparatus of the HP1100 series (Hewlett-Packard, Waldbronn, Germany) connected to a fluorescence detector (G1321A) was used; the system was controlled and the data evaluated with an HP-Chem-Station (Hewlett-Packard).

1 μL of the amino acid solution to be analysed was mixed in an automatic precolumn derivatization with 20 μL ortho-phthalaldehyde/2-mercaptoethanol ready-to-use reagent (Pierce Europe BV, Oud-Beijerland, The Netherlands). The fluorescent thio-substituted isoindoles formed here (Jones et al., Journal of Chromatography (1983) 266: 471–482) I.B.R. were separated over a combined precolumn (40×4 mm Hypersil ODS 5) and main column (Hypersil ODS 5, both columns from CS-Chromatographie Service GmbH, Langerwehe, Germany) with a gradient programme with an increasingly non-polar phase (methanol). The polar eluent was sodium acetate (0.1 molar, pH 7.2); the flow rate was 0.8 mL per minute.

Flourescence detection of the derivatized amino acids took place at an excitation wavelength of 230 nm and an emission wavelength of 450 nm. The glycine concentrations were calculated via a comparison with an external standard and asparagine as an additional internal standard.

The results of the enzyme test with threonine as the substrate are listed in table 2.

TABLE 2

| Strain | IPTG concentration (μM) | Serine hydroxymethyltransferase activity (nmol glycine/minute/mg protein) |
|---|---|---|
| ATCC13032/pZ1 | 0 | 0.9 |
| ATCC13032::pK18mobglyA' | 0 | 0.3 |
|  | 10 | 0.7 |
|  | 100 | 1.6 |

Example 5

Construction of the strain Brevibacterium flavum DM368-2::pK18mobglyA' with Reduced Regulatable glyA Expression By means of electroporation (Haynes et al., FEMS Microbiology Letters (1989) 61: 329–334) I.B.R., the blank vector pZ1 (Menkel et al., Applied and Environmental Microbiology (1989) 64: 549–554) I.B.R. and the plasmid pK18mobglyA' described in example 2 were introduced into the threonine-forming strain Brevibacterium flavum DM368-2. The strain DM368-2 is described in EP-B-0 385 940 and deposited as DSM5399.

After transformation with pZ1, the transformants were identified with the aid of their kanamycin resistance on LBHIS-agar plates containing 15 μg/mL kanamycin (Liebl et al., FEMS Microbiology Letters (1989) 65: 299–304) I.B.R. The plasmids were prepared from 3 of the transformants and checked for the presence of the pZ1 blank vector by restriction analysis. The control strain Brevibacterium flavum DM368-2/pZ1 was formed in this manner.

After transformation with pK18mobglyA' the plasmid had to integrate into the chromosome of Brevibacterium flavum DM368-2 via homologous recombination of the cloned 5' end of glyA. The kanamycin-resistant clones obtained were identified on LBHIS-agar plates containing 15 μg/mL kanamycin and 1 mM isopropyl β-D-thiogalactoside (Liebl et al., FEMS Microbiology Letters (1989) 65: 299–304) I.B.R.

Correct integration of pK18mobglyA' in the chromosome was checked in 4 resulting integration mutants by a polymerase chain reaction (PCR), as already described in example 3, with 100 ng chromosomal DNA of Brevibacterium flavum DM368-2::pK18mobglyA' as the template. The strain Brevibacterium flavum DM368-2::pK18mobglyA', in which the glyA gene is present under the control of the tac promoter which can be induced with isopropyl β-D-thiogalactoside (IPTG), was formed in this manner.

Example 6

Determination of the Serine Hydroxymethyltransferase Activity Coded by glyA in the Strain Brevibacterium flavum DM368-2::pK18mobglyA'

The crude extracts for the determination of the serine hydroxymethyltransferase activity coded by glyA in the strains B. flavum DM368-2/pZ1 and B. flavum DM368-2::pK18mobglyA' described in example 5 were obtained as already described in example 4. The protein determination in the cell-free crude extracts obtained and the discontinuous enzyme test, in which the glycine formed from the substrate threonine is quantified, was likewise carried out as described in example 4.

The results of this enzyme test with threonine as the substrate are listed in table 3.

TABLE 3

| Strain | IPTG concentration (μM) | Serine hydroxymethyltransferase activity (nmol glycine/minute/mg protein) |
|---|---|---|
| DM368-2/pZ1 | 0 | 1.6 |
| DM368-2::pK18mobglyA' | 0 | <0.1 |
|  | 10 | 0.8 |
|  | 100 | 1.7 |

Example 7

Preparation of L-threonine with Brevibacterium flavum

To investigate their threonine formation, the strains B. flavum DM368-2/pZ1 and DM368-2::pK18mobglyA' described in example 5 were precultured in 100 mL Brain Heart Infusion Medium (Difco Laboratories, Detroit, USA) with 25 μg kanamycin/mL and 100 μM isopropyl β-D-thiogalactoside (IPTG) for 14 hours at 30° C. The cells were then washed once with 0.9%(w/v) sodium chloride solution and 60 mL portions of CgXII medium were inoculated with this suspension such that the $OD_{600}$ (optical density at 600 nm) was 0.5. The medium was identical to the medium described by Keilhauer et al. (Journal of Bacteriology (1993) 175: 5593–5603), but additionally comprised 25 μg kanamycin/mL and 0, 10 or 100 μM isopropyl β-D-thiogalactoside (IPTG).

Culturing of the two strains was carried out at 30° C. over a period of 72 hours. After 48 and 72 hours samples were in each case taken and the cells were centrifuged off briefly (5 minutes at 13000 revolutions per minute with a Biofuge pico from Heraeus, Osterode, Germany).

The quantitative determination of the extracellular amino acid concentrations from the culture supernatant was carried out as already described in example 4 by means of reversed phase HPLC (Lindroth et al., Analytical Chemistry (1979) 51: 1167–1174) I.B.R. The threonine concentrations were calculated via a comparison with an external standard and asparagine as an additional internal standard.

The results are listed in table 4.

TABLE 4

| Strain | IPTG concentration µM | L-Threonine (g/l) 48 hours | 72 hours |
|---|---|---|---|
| DM368-2/pZ1 | 0 | 1.27 | 1.32 |
| DM368-2::pK18mobglyA' | 10 | 1.32 | 1.44 |
|  | 0 | 1.41 | 1.60 |

The abbreviations and designations used have the following meaning.

BamHI: Restriction endonuclease from *Bacillus amyloliquefaciens*
BglII: Restriction endonuclease from *Bacillus globigii*
BstEII: Restriction endonuclease from *Bacillus stearothermophilus*
EcoRI: Restriction endonuclease from *Escherichia coli*
EcoRV: Restriction endonuclease from *Escherichia coli*
HindIII: Restriction endonuclease from *Haemophilus influenzae*
SacI: Restriction endonuclease from *Streptomyces achromogenes*
kan: Kanamycin resistance gene
lacI$^q$: Gene for the repressor of the tac promoter Ptac
Ptac: tac promoter
glyA': 5' part of the serine hydroxymethyltransferase gene
glyA2-reverse: Primer for checking an integration
RSP: Reverse standard primer for checking an integration Further variations and modifications of the present invention will be apparent to those skilled in the art from a reading of the foregoing and are encompassed by the claims appended hereto.

German patent application 199 59 329.9 I.B.R. is relied upon and incorporated herein by reference.

We claim:

1. A process for the preparation of an L-amino acid, comprising fermenting an L-amino acid-producing coryneform bacteria in which at least the glyA gene is attenuated to thereby produce said amino acid, wherein said amino acid is L-threonine or L-isoleucine.

2. The process according to claim 1, and further comprising concentrating the L-amino acid in a medium or in the cells for the bacteria.

3. The process according to claim 1, wherein expression of a polynucleotide, which codes for the glyA gene, is reduced.

4. The process according to claim 1, wherein a catalytic property of the polypeptide for which the polynucleotide glyA codes is reduced.

5. The process according to claim 1, further comprising an integration mutagenesis step utilizing the vector pK18mobglyA' to achieve attenuation.

6. The process according to claim 1, wherein for the preparation of L-threonine, bacteria in which one or more genes selected from the group consisting of:

1) the hom gene which codes for homoserine dehydrogenase,
   2) the gap gene which codes for glyceraldehyde 3-phosphate dehydrogenase,
   3) the pyc gene which codes for pyruvate carboxylase,
   4) the mqo gene which codes for malate:quinone oxidoreductase, and
   5) the thrE gene which codes for threonine export, is/are over-expressed at the same time the bacteria are fermented.

7. The process according to claim 1, wherein for the preparation of L-threonine, bacteria in which one or more genes selected from the group consisting of:

1) the pck gene which codes for phosphoenol pyruvate carboxykinase, and
   2) the poxB gene which codes for pyruvate oxidase is/are attenuated at the same time the bacteria are fermented.

8. The process according to claim 1, wherein a microorganism of the genus Corynebacterium is employed.

9. The process according to claim 2, and further comprising isolating the L-amino acid.

10. The process according to claim 8, wherein the Corynebacterium is of the species *glutamicum*.

11. A Coryneform bacteria wherein the glyA gene is attenuated.

12. The plasmid pK18mobglyA'.

* * * * *